United States Patent
Zhang et al.

(10) Patent No.: US 10,077,292 B2
(45) Date of Patent: Sep. 18, 2018

(54) FORMALDEHYDE-FREE PROTEINACEOUS BINDER COMPOSITIONS

(71) Applicant: JOHNS MANVILLE, Denver, CO (US)

(72) Inventors: Mingfu Zhang, Highlands Ranch, CO (US); Jawed Asrar, Englewood, CO (US); Uranchimeg Lester, Littleton, CO (US)

(73) Assignee: Johns Maville, Denver, CO (US)

( * ) Notice: Subject to any disclaimer, the term of this patent is extended or adjusted under 35 U.S.C. 154(b) by 39 days.

(21) Appl. No.: 14/529,196

(22) Filed: Oct. 31, 2014

(65) Prior Publication Data

US 2015/0050857 A1     Feb. 19, 2015

Related U.S. Application Data

(62) Division of application No. 13/410,470, filed on Mar. 2, 2012, now Pat. No. 8,901,017.

(51) Int. Cl.
  *D03D 15/00*   (2006.01)
  *C07K 16/00*   (2006.01)
  (Continued)

(52) U.S. Cl.
  CPC .............. *C07K 14/415* (2013.01); *B05D 1/02* (2013.01); *B05D 1/18* (2013.01); *B05D 1/28* (2013.01); *B05D 1/305* (2013.01); *C07C 211/09* (2013.01); *C07H 3/02* (2013.01); *C08J 3/24* (2013.01); *C08J 5/24* (2013.01); *C08K 5/053* (2013.01);
  (Continued)

(58) Field of Classification Search
  USPC ...... 442/181; 428/292.1; 530/409, 375, 376, 530/362, 357, 354, 356, 374; 525/54.1
  See application file for complete search history.

(56) References Cited

U.S. PATENT DOCUMENTS 5,401,812 A * 3/1995 Yamamoto ............ C08L 79/085
                                                          525/425
8,901,017 B2 * 12/2014 Zhang ........................ C08J 3/24
                                                          428/292.1

(Continued)

FOREIGN PATENT DOCUMENTS

EP       2 354 205 A1    8/2011

*Primary Examiner* — Lynda Salvatore
(74) *Attorney, Agent, or Firm* — Robert D. Touslee

(57) ABSTRACT

Binder compositions are described, where the compositions include a protein, a first crosslinking compound that includes a carbohydrate, and a second crosslinking compound that includes two or more primary amine groups. The first and second crosslinking compounds may be individually crosslinkable with each other and with the protein. Also described are fiber products that may include inorganic or organic fibers and a cured thermoset binder prepared from a protein and at least two crosslinking compounds. Additionally, methods of making fiber products are described that include providing inorganic or organic fibers, and applying a liquid binder composition to the fibers to form a fiber-binder amalgam. The liquid binder composition may include a protein and at least two crosslinking compounds that include a carbohydrate and an organic amine with two or more primary amines. The amalgam may be heated to a curing temperature to form the fiber product.

20 Claims, 1 Drawing Sheet

(51) Int. Cl.
| | |
|---|---|
| *A61K 36/00* | (2006.01) |
| *D04H 1/00* | (2006.01) |
| *C07K 14/415* | (2006.01) |
| *C08J 3/24* | (2006.01) |
| *C08J 5/24* | (2006.01) |
| *C09J 189/00* | (2006.01) |
| *B05D 1/02* | (2006.01) |
| *B05D 1/18* | (2006.01) |
| *B05D 1/28* | (2006.01) |
| *B05D 1/30* | (2006.01) |
| *C07C 211/09* | (2006.01) |
| *C07H 3/02* | (2006.01) |
| *C08K 5/053* | (2006.01) |
| *C08K 5/17* | (2006.01) |
| *C08K 5/18* | (2006.01) |

(52) U.S. Cl.
CPC .................. *C08K 5/17* (2013.01); *C08K 5/18* (2013.01); *C09J 189/00* (2013.01); *B05D 2203/35* (2013.01); *B05D 2256/00* (2013.01); *C08J 2389/00* (2013.01); *Y10T 428/249924* (2015.04); *Y10T 442/2992* (2015.04); *Y10T 442/30* (2015.04); *Y10T 442/60* (2015.04)

(56) References Cited

U.S. PATENT DOCUMENTS

| | | | |
|---|---|---|---|
| 2007/0088114 A1* | 4/2007 | Asgari | A61K 9/1664 524/431 |
| 2009/0169867 A1 | 7/2009 | Kelly | |
| 2011/0189479 A1 | 8/2011 | Zhang et al. | |
| 2012/0058701 A1 | 3/2012 | Zhang et al. | |
| 2013/0140481 A1* | 6/2013 | Naerum | C03C 25/26 252/62 |

* cited by examiner

FORMALDEHYDE-FREE PROTEINACEOUS BINDER COMPOSITIONS

CROSS-REFERENCE TO RELATED APPLICATION

This application is a division of prior U.S. application Ser. No. 13/410,470 filed Mar. 2, 2012 now U.S. Pat. No. 8,901,017. The entire contents of the above-identified application is incorporated herein by reference for all purposes.

BACKGROUND OF THE INVENTION

Manufacturers of fiberglass containing products continue the search for commercially acceptable substitutes to traditional, formaldehyde-containing binder compositions. Health concerns about the irritant, allergenic, and possibly carcinogenic effects of off-gassing formaldehyde from of traditional phenol-formaldehyde and urea-formaldehyde binders in articles a diverse as building insulation, furniture upholstery, and textiles have prompted the industry to search for formaldehyde-free alternatives. However, presently available alternatives have their own challenges in terms of ease of manufacture, process emission, flame resistance, moisture resistance, sustainability, and cost, among other challenges.

One class of formaldehyde-free binder compositions relies on esterification reactions between carboxylic acid groups in polycarboxy polymers and hydroxyl groups in alcohols. Water is the main byproduct of these covalently crosslinked esters, which makes these binders more environmentally benign, as compared to traditional formaldehyde-based binders. However, these formaldehyde-free binder compositions also make extensive use of non-renewable, petroleum-based ingredients. Thus, there is a need for formaldehyde-free binder compositions that rely less on petroleum-based ingredients.

There are also formaldehyde-free binder formulations based on renewable carbohydrates, such as reducing sugars. These binders contain significant amount of renewable raw materials; therefore are more sustainable than petroleum-based binders. Unfortunately, these sugar-based binders generate high VOC (volatile organic compound) emissions during thermal curing. The high VOC emission of these binders limits their uses in applications such as fiberglass insulation, due to the ever-tightening emission permit limits in manufacturing facilities. Therefore, there is a need for sustainable formaldehyde-free binder compositions that emit low VOC emissions during thermal curing.

As an abundant and renewable material, protein has great potential to be an alternative to petroleum-based binders. Proteins are already used extensively as a component of adhesives for various substrates. However, many types of protein-containing adhesives have poor gluing strength and water resistance. Thus, there is a need to improve the bonding strength and water resistance of protein-containing binder compositions to levels that are similar to or better than those of conventional, petroleum-based binder compositions. These and other issues are addressed in the present Application.

BRIEF SUMMARY OF THE INVENTION

Embodiments of the invention include binder compositions that are made from a protein and at least two crosslinking compounds. A first crosslinking compound may include a carbohydrate, such as a reducing sugar. A second crosslinking compound may include an organic amine with two or more primary amine groups. The first and second crosslinking compounds may be individually crosslinkable with each other and with the protein.

Embodiments of the invention further include a fiber product having inorganic and/or organic fibers and a cured thermoset binder prepared from a binder composition. The binder composition may be made from a protein and at least two crosslinking compounds, where the first crosslinking compound may include a carbohydrate, such as a reducing sugar, and the second crosslinking compound may include an organic amine with two or more primary amine groups. The first and second crosslinking compounds may be individually crosslinkable with each other and with the protein.

Embodiments of the invention further include methods of making a fiber product. The methods may include the step of providing fibers made from inorganic fibers, organic fibers, or both. A liquid binder composition may be applied to the fibers to form a fiber-binder amalgam. The liquid binder composition may be made from a protein, such as a soy protein, a first crosslinking compound that may include a carbohydrate, and a second crosslinking compound that may include an organic amine having two or more primary amine groups. The first and second crosslinking compounds may be individually crosslinkable with each other and with the protein. The method may further include the step of heating the fiber-binder amalgam to a curing temperature of 100° C. to 300° C. to form the fiber product.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sublabel is associated with a reference numeral and follows a hyphen to denote one of multiple similar components. When reference is made to a reference numeral without specification to an existing sublabel, it is intended to refer to all such multiple similar components.

DETAILED DESCRIPTION OF THE INVENTION

Figure 1:
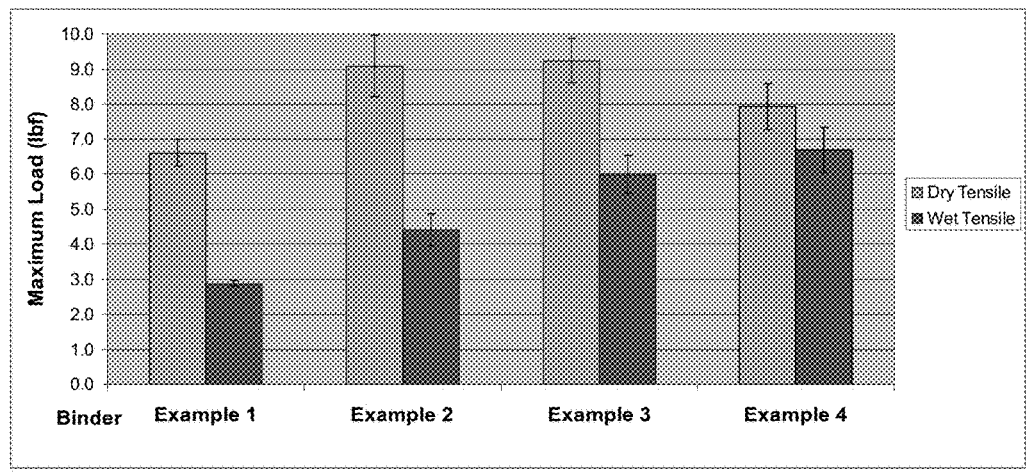
FIG. 1 is a graph of handsheet tensiles for the binder compositions described in Examples 1-4.

Binder compositions are described that include renewable materials such as proteins in combination with two or more other binder components. Examples include binder compositions made from at least one protein and at least two or more crosslinking compounds, where the protein and crosslinking compounds are all crosslinkable with each other. The term "crosslinkable" refers to the ability of two compounds to form covalent bonds with each other, although other type of bonds may also be formed between the compounds. The binder compositions may also optionally include additional components such as cure catalysts.

Binder solutions made from the present binder compositions may be applied to a substrate such as inorganic and/or organic fibers and cured to make a composite of the thermoset binder and substrate such as a building material (e.g., fiberglass insulation). These materials do not off-gas formaldehyde during their production and use, or decompose to contaminate factories, buildings, homes, and other areas with formaldehyde. Furthermore, the binder compositions may at least partially substitute renewable compounds (e.g., proteins) for non-renewable compounds such as petroleum-based compounds. For example, the binder compositions may include reduced amounts of petroleum-based compounds such as unsaturated carboxylic acid monomers, carboxy acid monomers, and/or sulfonic acid monomers. In further examples, the present binder compositions may include no unsaturated carboxylic acid monomers (e.g., (meth)acrylic acid, crotonic acid, itaconic acid, 2-methyl itaconic acid, a, 3-methylene glutaric acid, monoalkyl fumarates, maleic acid, etc.), carboxy acid monomers, and/or sulfonic acid monomers.

Exemplary Binder Compositions:

Exemplary binder compositions may include compositions containing at least one protein and two or more crosslinking compounds, where the protein and crosslinking compounds are all crosslinkable with each other. The proteins used in the binder compositions may include vegetable and/or animal proteins. These proteins may be readily available from a renewable source. Examples of proteins that may be used in the binder compositions include soy protein, wheat protein, corn protein, whey protein, albumin, keratin, gelatin, collagen, gluten, and casein, among other kinds of proteins.

The proteins may be used in an unmodified, un-denatured state (i.e., native proteins). Alternatively, the proteins may be modified and/or denatured using physical, chemical, or enzymatic methods that cause changes to the primary, secondary, tertiary, and/or quaternary structures of the proteins. These methods may include denaturing the proteins to change their secondary, tertiary and quaternary structures, and chemically or enzymatically breaking down the protein molecules into smaller fragments. They may also include modifying the pendant moieties of the protein, such as adding additional carboxyl groups to the protein molecules.

One example of a protein used in the present binder compositions may be soy protein in the form of a soy flour, soy protein concentrate, soy protein isolate, and/or soy polymer, among other forms of soy protein. Soy flour may be produced by grinding soybeans into a powder. Soy flour may retain the natural oils and other compounds from the soybeans, or may be defatted to produce flour with a higher protein content (e.g., about 50 wt % protein or more). Soy protein concentrate contains about 70 wt % soy protein and is made by removing water soluble carbohydrates from defatted soy flour. Soy protein isolate is a highly refined, purified form of soy protein with the protein content of about 90 wt. % or more. The isolates may be made from defatted soy flour that has most of the non-protein soybean components removed (e.g., fats, carbohydrates, etc.). Soy polymers may include soy proteins that have been chemically modified to impart a variety of functionalities to protein molecules.

The soy protein may be denatured/modified to unfold protein molecules in the dispersion. Upon unfolding, the functionalities of protein molecules (e.g., carboxyl and amine) are exposed and may actively react with other binder ingredients to form crosslinking bonds. Examples of protein denaturation and modification methods include, but are not limited to, heat treatment, treatment with chaotropic agents (e.g., urea, guanidinium chloride, and lithium perchlorate), acids, bases, metal salts, alcohols, detergents, thiols, sulfites, and mixtures thereof.

The soy protein may also be modified to reduce the viscosity of soy protein dispersion, therefore reducing the viscosity of protein-based thermoset binder compositions. Examples of methods of reducing the viscosity of soy protein dispersion include, but are not limited to, hydrolyzing protein using enzymes or alkalis and cleaving disulfide bonds in protein by thiols or sulfites. For example, the viscosity of soy protein dispersion may be reduced by the treatment with sodium bisulfite.

Soy protein such as soy flour may be dispersed or dissolved in water. Other binder ingredients, such as the crosslinking compounds, may be mixed with the aqueous soy protein dispersion or solution to form the final binder composition that is applied to the fibrous products.

The relative amount of protein added to the binder compositions can vary depending on other binder components used, the processing conditions, and the type of end product being made, among other considerations. Embodiments have the concentration of the protein component (as a percentage weight of the total solids of the binder composition) ranging from about 50% to about 95%; about 55% to about 90%, about 60% to about 85%; about 65% to about 80%; etc.

One example of a crosslinking compound used in the present binder compositions may be a carbohydrate, such as a reducing sugar. A reducing sugar may be any sugar that has an aldehyde group or is capable of forming an aldehyde in solution through isomerization. Exemplary reducing sugars may include monosaccharides, such as glucose, fructose, glyceraldehyde, and galactose, and disaccharides, such as lactose and maltose.

Another example of a crosslinking compound that may be used in the present binder compositions is a compound containing multiple primary amine groups. Primary amines can be more reactive than secondary, tertiary, or quaternary amines for crosslinking reactions with the protein and/or carbohydrate components of the binder compositions. Multiple primary amine groups in the crosslinking compound may increase the crosslinking density in the cured binder composition. Exemplary amine-containing crosslinking compounds include organic amines having two to five primary amine groups. Exemplary organic amines having two primary amine groups include aliphatic diamines such as ethylenediamine, propane-1,3-diamine, butane-1,4-diamine, pentane-1,5-diamine, and hexamethylenediamine. The present binder compositions may also include aromatic polyamines having two or more primary amine groups such as xylylenediamine.

The crosslinking compounds may comprise about 5 wt. % to about 50 wt. %, of the binder composition. In certain embodiments, the crosslinking compounds may comprise about 10 wt. % to about 45 wt. %, about 15 wt. % to about 40 wt. %, about 20 wt. % to about 35 wt. %, etc. of the binder composition.

The binder compositions may also optionally include a cure catalyst. Examples of cure catalysts may include ammonium salts of inorganic acids. For example, the cure catalyst may be ammonium sulfate, ammonium phosphate, ammonium nitrate, ammonium chloride, etc. Examples of cure catalysts may also include Lewis acids. For example, Lewis acid catalyst may be selected from sulfates, nitrates, halides, and phosphates of aluminum, zinc, iron, copper, magnesium, tin, zirconium, and titanium. Lewis acid catalysts may also include organic titanates and zirconates. A combination of catalysts, such as the combination of a Lewis acid and an ammonium salt of inorganic acid may be used. The cure catalyst may be added to expedite curing of the binder composition.

The binder compositions may also optionally include extenders. Examples of extenders may include starch, lignin, rosin, among other extenders.

The binder compositions may have a neutral or alkaline pH. For example, the pH of the present binder compositions may be greater than or equal to 7 (e.g., 7 or more, 8 or more, 9 or more, 9.5 or more, 10 or more, 10.5 or more, etc). The neutral or alkaline pH of the binder compositions reduces the corrosion of process equipment associated with binder transportation, storage, and application.

The protein in the binder composition may be actively crosslinkable with the crosslinking compounds. The protein may be treated to expose the reactive moieties on polypeptide chains of the proteins for crosslinking reactions. For example, amino groups from the amino-containing amino acid moities on protein chains (e.g., lysine, arginine) and the N-termini of polypeptide chains may react with aldehyde groups of the reducing sugar compound. Similarly, carboxyl groups from carboxyl-containing amino acid moities (e.g., aspartic acid, glutamic acid) and the C-termini of polypeptide chains may react with amine groups on the organic amine compound to actively crosslink the protein in the binder composition. In addition, the two crosslinking compounds may crosslink with each other by the reaction between aldehyde groups and amine groups.

Stable, one-part binder compositions of the present embodiments may be formulated by mixing a protein component, a carbohydrate (e.g., a reducing sugar), a compound with multiple primary amine groups, and optionally catalysts and additives, in aqueous media. The formulated one-part binder compositions may undergo very little covalent crosslinking reactions under ambient conditions (e.g., room temperature). However, at elevated temperatures, such as upon thermal curing, the formulated one-part binder compositions may undergo crosslinking reactions to produce a cured thermoset binder having superior mechanical strength and water resistance as compared to the binder compositions with no crosslinking compounds as shown in FIG. 1. Additionally, as shown in FIG. 1, the crosslinking density in the cured binder compositions of the present embodiments may be higher than in binder compositions where only one crosslinking compound (e.g., a reducing sugar) is used with the protein component.

Methods of Making Fiber Products:

The present binder compositions may be used in methods of making fiber products. The methods may include applying a liquid binder to fibers and curing the binder composition on the fibers to form the fiber product. The liquid binder may be spray coated, spin coated, curtain coated, knife coated, or dip coated onto fibers. Once the liquid binder composition is applied, the binder and substrate may be heated to cure the binder composition and form a composite of cured binder and fibers that make up the fiber product.

The liquid binder may be formed to have a viscosity in range that permits the efficient application of the solution to the fibers. For example, the viscosity may be about 1 centipoise to about 1000 centipoises when the liquid binder is at room temperature.

If the viscosity of the liquid binder applied to the substrate is too high, it may slow down the application process both at the release point for the binder as well as the rate of mixing and coverage of the binder on the substrate. Solutions and dispersions of many types of protein, including some types of soy protein in aqueous solutions, have generally high viscosities. Thus, the present protein-containing binder compositions may include proteins with a relatively low viscosity when dissolved/dispersed in the liquid binder. These may include soy proteins that are modified to lower the viscosity of soy protein dispersion.

After application of the liquid binder composition on the substrate, the amalgam of liquid binder and substrate undergoes curing. In the curing process the protein and the crosslinking compounds may form covalent bonds among each other to convert the amalgam into a thermoset composite. When a thermal curing process is used, the amalgam may be subjected to an elevated temperature (e.g., between 100° C. and 300° C.) to facilitate crosslinking in the binder. The peak curing temperature may depend on the specific formulation of the protein-containing binder composition, the substrate, and whether a cure catalyst is used. The cured material typically includes about 0.5 wt % to about 50 wt % thermoset binder composition (e.g., about 1 wt. % to about 10 wt. %) with the substrate representing most of the remaining weight.

The binder composition may be a stable one-part, pre-mixed mixture that can be recycled during the application to the fibers and/or between applications on fibers. Thus, an unused portion of the binder that, for example, passes through the fibers may be captured and sent back to the supply of binder applied to the fibers. In some embodiments, the unused portion of the binder may be purified or otherwise treated before returning to the supply.

The reuse of the binder may not only reduce the amount of binder used, it may also reduce the amount of waste materials that must be treated and discarded. However, recycling unused binder requires that the binder remain stable for two or more application cycles. In many instances, two-part soy binder compositions that mix separated and highly reactive components immediately before their application cure too rapidly to be recycled. One-part binder compositions may also be unsuitable if they do not have a sufficient pot life to remain relatively unreacted prior to use and during recycling. The present binder compositions include pre-mixed, one-part binder compositions that are stable enough to be appropriate for binder recycling. The pre-mixed, one-part mixtures may also have a shelf life of at least one month.

Fiber Products:

The present binder compositions may be added to fibers to produce composite fiber products. The fibers may include organic fibers and/or inorganic fibers. For example, the fibers may include polymer fibers and/or glass fibers, among other types of fibers. The fibers may be arranged as an insulation batt, woven mat, non-woven mat, or spunbond product etc.

The present binder compositions may be used in fiber products to make insulation and fiber-reinforced composites, among other products. The products may include fibers (e.g., organic and/or inorganic fibers) contained in a cured thermoset binder prepared from a one-part binder composition of a carbohydrate, a compound having two or more primary amine groups, and a protein crosslinkable with both the carbohydrate and the compound having two or more primary amine groups.

The fibers may include glass fibers, carbon fibers, and organic polymer fibers, among other types of fibers. For example, the combination of the binder composition and glass fibers may be used to make fiberglass insulation products. Alternatively, when the fiberglass is a microglass-based substrate, the binder may be applied and cured to form printed circuit boards, battery separators, filter stock, and reinforcement scrim, among other articles.

EXPERIMENTAL

The following Examples are presented to provide specific representative embodiments of the present invention. It should be understood, however, that the invention is not limited to the specific details as set forth in these Examples.

Example #1: Preparation of Soy Flour Dispersion

To a flask equipped with a mechanical stirrer were added 748.0 grams of de-ionized water and 2.0 grams of sodium bisulfite. After the dissolution of sodium bisulfite, 200.0 grams of defatted soy flour (Cargill Prolia 200/90, containing 5% moisture) were added under constant stirring. The resulting soy flour dispersion has a soy flour content of 20% by weight.

Example #2: Preparation of a Binder Composition of Soy Flour and Dextrose

To a flask containing 100.0 grams of the soy flour dispersion of Example 1 were added 14.66 grams of dextrose monohydrate and 1.67 grams of ammonium sulfate. The mixture was stirred until the dextrose and ammonium sulfate were fully dissolved. The resulting binder has a w/w ratio of soy flour to dextrose of 60/40.

Example #3: Preparation of a Binder Composition of Soy Flour, Dextrose, and Hexamethylenediamine To a flask containing 17.6 grams of water were added 4.65 grams of 70% hexamethylenediamine solution (i.e., 28.0 mmol of hexamethylenediamine) and 11.09 grams of dextrose monohydrate (i.e., 56.0 mmol of dextrose). After dissolution of the dextrose under stirring, 100.0 grams of the soy flour dispersion of Example 1 and 1.67 grams of ammonium sulfate were added. The mixture was stirred until a homogeneous mixture was obtained. The resulting binder has a w/w ratio of soy flour to the crosslinker combination (i.e., dextrose and hexamethylenediamine) of 60/40, and a molar ratio of dextrose to hexamethylenediamine of 2.0/1.0.

Example #4: Preparation of a Binder Composition of Soy Flour, Dextrose, and Hexamethylenediamine To a flask containing 17.77 grams of water were added 3.91 grams of 70% hexamethylenediamine solution (i.e., 23.55 mmol of hexamethylenediamine) and 11.66 grams of dextrose monohydrate (i.e., 58.83 mmol of dextrose). After dissolution of the dextrose under stirring, 100 grams of the soy flour dispersion of Example 1 and 1.67 grams of ammonium sulfate were added. The mixture was agitated until a homogeneous mixture was obtained. The resulting binder has a w/w ratio of soy flour to the crosslinker combination (i.e., dextrose and hexamethylenediamine) of 60/40, and a molar ratio of dextrose to hexamethylenediamine of 2.5/1.0.

Comparative Example #1: Preparation of a Binder Composition of Dextrose and Hexamethylenediamine To a flask containing 182.06 grams of water were 16.6 grams of 70% hexamethylenediamine solution (i.e., 100.0 mmol of hexamethylenediamine). Into the diluted hexamethylenediamine solution were dissolved 39.64 grams of dextrose monohydrate (i.e., 200 mmol of dextrose). The resulting binder has a molar ratio of dextrose to hexamethylenediamine of 2.0/1.0 and a solids content of 20%.

Comparative Example #2: Preparation of a Binder Composition of Dextrose and Ammonium Citrate To a flask containing 518.96 grams of water were added 24.32 grams of ammonium citrate tribasic (i.e., 100.0 mmol of ammonium citrate) and 118.92 grams of dextrose monohydrate (i.e., 600.0 mmol of dextrose). The mixture was agitated until a clear solution was obtained. The resulting binder has a molar ratio of dextrose to ammonium citrate of 6.0/1.0 and a solids content of 20%.

Handsheet Tensile Test

The soy binder compositions of Examples 1-4 were evaluated via the handsheet tensile test method. Binder compositions were prepared from the binders of Examples 1-4 by first diluting them to a solids content of 3%, and then adding 1% (by weight based on the total solids of binder) of gamma-aminopropyltriethoxysilane (Silquest A-1100, Momentive). Glass microfiber filter paper sheets (8"×10", Catalog No. 1820-866, Whatman) were then dip-coated with the binder compositions. The coated sheets were then dried and cured at 210° C. for 3 minutes in a Mathis oven.

Thereafter, the coated sheets were cut to 1"×4" stripes for tensile tests. For each binder composition, ten 1"×4" stripes were used for dry tensile tests and another ten 1"×4" stripes were used for wet tensile tests. Samples for wet tensile tests were immersed in 82.2° C. (180° F.) water for 10 min, and then cooled down before testing. Tensile tests were conducted on an Instron tensile testing machine.

Table 1 and FIG. 1 show the tensile strengths for the binder compositions described in Examples 1-4. The mean tensile strength represents the average tensile strength of ten specimens for each binder composition. The error bars shown in FIG. 1 represent the standard deviation.

TABLE 1

Tensile strength tests of glass microfiber filter papers coated with binder compositions of Examples 1-4.

| | Binder Composition | | | Tensile (lbf) | | | | |
| | Soy Flour/ | | | Dry | | Wet | | |
| Binder No. | Crosslinker (w/w) | Crosslinker | Binder Add-on | Mean | Standard Deviation | Mean | Standard Deviation | Wet Tensile Retention |
|---|---|---|---|---|---|---|---|---|
| Example 1 | 100/0 | None | 12.97% | 6.60 | 0.39 | 2.88 | 0.07 | 43.6% |
| Example 2 | 60/40 | Dextrose | 13.29% | 9.09 | 0.87 | 4.40 | 0.46 | 48.4% |
| Example 3 | 60/40 | Dextrose/Hexamethylenediamine (Molar ratio = 2.0/1.0) | 12.97% | 9.24 | 0.63 | 5.98 | 0.53 | 64.8% |
| Example 4 | 60/40 | Dextrose/Hexamethylenediamine (Molar ratio = 2.5/1.0) | 12.74% | 7.92 | 0.66 | 6.68 | 0.64 | 84.3% |

Wet tensile strength from the handsheet tests is a good indication of crosslinking density. Table 1 and FIG. 1 show that the soy binder compositions with crosslinking compounds have higher wet tensile strengths than the soy binder compositions that do not have crosslinking compounds. For example, the wet tensile strength of the neat soy flour binder composition (Example 1) is 2.88 lbf only, indicating its poor water resistance. When dextrose is added as a crosslinking compound (Example 2), the wet tensile strength increases to 4.40 lbf, which indicates some increase in crosslinking density. When the second crosslinking compound, hexamethylenediamine, is added to the binder compositions (Examples 3 and 4), the wet tensile strength significantly increases and yields values of 5.98 and 6.68 lbf, respectively. These wet tensile strengths show that the combination of two crosslinking compounds significantly increase the crosslinking density of the binder compositions.

As shown in Table 1, the wet tensile retentions of the soy binder compositions with two crosslinking compounds (Examples 3-4) are significantly higher than the soy flour binders containing no crosslinker (Example 1) or with dextrose only (Example 2). The high wet tensile retention of the soy binders with two crosslinking compounds indicates that the binder compositions of the present embodiments have excellent water resistance.

Tube Furnace Test

Liquid binder samples were tested for volatile organic carbon (VOC) emission via the tube furnace method. For each binder composition, 0.5 grams of a liquid binder sample with a solid content of 20% was coated onto a piece of glass microfiber filter (Whatman, Grade GF/A); and the filter was then placed into a tube furnace that was preheated to 232° C. (450° F.). VOC emission during thermal curing was drawn through a heated line (set at 130° C.) to a flame ionization detector (FID) analyzer. The readings (in ppm) from the FID analyzer were recorded at 15-second interval.

Figure 2:
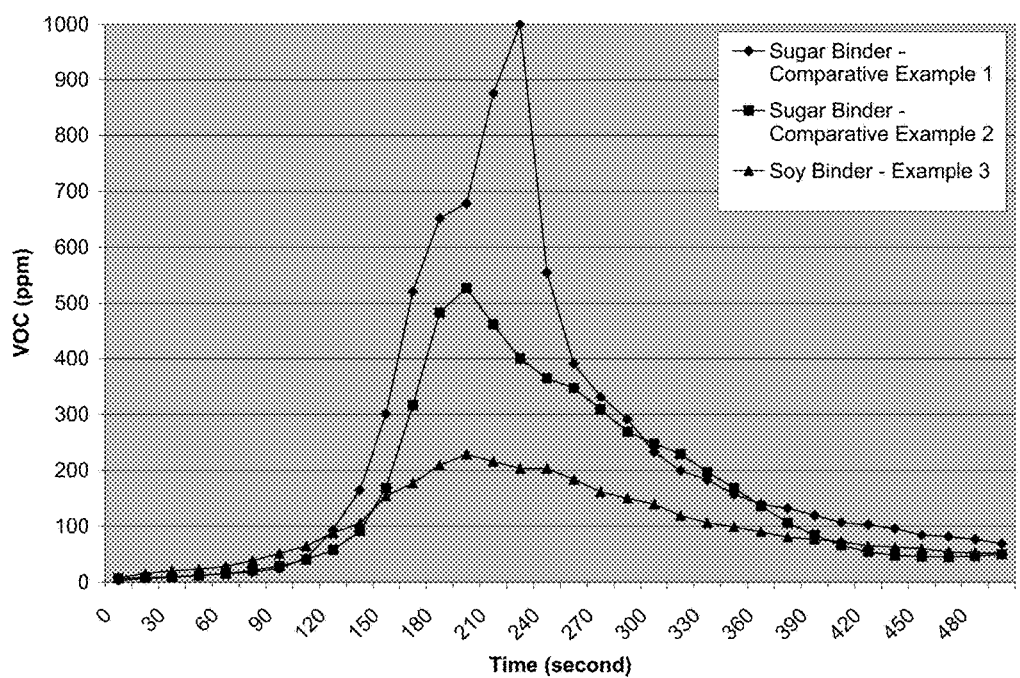
FIG. 2 is a graph of VOC emission at the cure temperature of 232° C., determined by the tube furnace method, of the binder compositions described in Example 3 and Comparative Examples 1-2.

As shown in FIG. 2, the soy binder of Example 3 has significantly lower VOC emission than the two sugar binders of Comparative Examples 1-2. For example, the measured peak VOC readings are 1,000 ppm, 527 ppm, and 228 ppm for the dextrose-hexamethylenediamine binder (Comparative Example 1), the dextrose-ammonium citrate binder (Comparative Example 2), and the soy binder (Example 3), respectively. The low-emitting soy binder compositions of the present invention have a significant advantage over high-emitting formaldehyde-free binders in meeting constantly increasing environmental standards.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the protein" includes reference to one or more proteins and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:
1. A fiber product comprising:
    inorganic or organic fibers and a cured thermoset binder prepared from a binder composition comprising:
    a protein;
    a first crosslinking compound comprising a carbohydrate, wherein the carbohydrate comprises a reducing sugar; and
    a second crosslinking compound comprising two or more primary amine groups, wherein the first and second crosslinking compounds are individually crosslinkable with each other and with the protein.

2. The fiber product of claim 1, wherein the inorganic or organic fibers comprise glass fibers.

3. The fiber product of claim 1, wherein the fiber product is selected from the group consisting of an insulation batt, a woven or non-woven fiberglass mat, and a spunbond product.

4. The fiber product of claim 1, wherein the protein comprises soy protein, and the second crosslinking compound comprises an organic diamine having two primary amine groups.

5. A method of making a fiber product, the method comprising:
providing fibers comprising inorganic or organic fibers;
applying a liquid binder composition to the fibers to form a fiber-binder amalgam, wherein the liquid binder composition comprises:
  a protein;
  a first crosslinking compound comprising a carbohydrate, wherein the carbohydrate comprises a reducing sugar; and
  a second crosslinking compound comprising two or more primary amine groups,
  wherein the first and second crosslinking compounds are individually crosslinkable with each other and with the protein; and
heating the fiber-binder amalgam to a curing temperature of 100 C to 300 C to form the fiber product.

6. The method of claim 5, wherein the liquid binder composition comprises a pre-mixed, one-part mixture.

7. The method of claim 6, wherein the liquid binder composition has a shelf life of at least one month.

8. The method of claim 5, wherein the protein comprises soy protein, and the second crosslinking compound comprises an organic diamine having two primary amine groups.

9. The fiber product of claim 1, wherein the reducing sugar comprises glucose, fructose, galactose, lactose, or maltose.

10. The fiber product of claim 1, wherein the reducing sugar comprises dextrose.

11. The fiber product of claim 1, wherein the binder composition further comprises a cure catalyst.

12. The fiber product of claim 11, wherein the cure catalyst comprises a salt of an inorganic acid.

13. The fiber product of claim 1, wherein the cured thermoset binder comprises 1 wt. % to 10 wt. % of a total weight of the fiber product.

14. The method of claim 5, wherein the reducing sugar comprises glucose, fructose, galactose, lactose, or maltose.

15. The method of claim 5, wherein the reducing sugar comprises dextrose.

16. The method of claim 5, wherein the liquid binder composition further comprises a cure catalyst.

17. The method of claim 16, wherein the cure catalyst further comprises a salt of an inorganic acid.

18. The method of claim 5, wherein the fiber product comprises a cured thermoset binder that comprises 1 wt. % to 10 wt. % of a total weight of the fiber product.

19. The fiber product of claim 1, wherein the second crosslinking compound comprises ethylenediamine, propane-1,3-diamine, butane-1,4-diamine, pentane-1,5-diamine, hexamethylenediamine, or xylylenediamine.

20. The fiber product of claim 19, wherein:
the reducing sugar comprises glucose, fructose, galactose, lactose, or maltose,
the protein is from 50 wt. % to 95 wt. % of the binder composition on a total solids basis,
the first crosslinking compound and the second crosslinking compound sum to from 5 wt. % to 50 wt. % of the binder composition on a total solids basis.

* * * * *